United States Patent

Mulders et al.

[11] Patent Number: 5,824,804
[45] Date of Patent: Oct. 20, 1998

[54] METHOD FOR THE PREPARATION OF A N-ALKOXY-(TETRA-OR HEXAHYDRO)-PHTHALIMIDE AND METHOD FOR THE PREPARATION OF A N-ALKOXYAMINE

[75] Inventors: Joannes M. C. A. Mulders, Geleen, Netherlands; Dominique M. C. Callant, Houthalen, Belgium; Anna M. C. F. Castelijns, Beek, Netherlands

[73] Assignee: DSM N.V., TE Heerlen, Netherlands

[21] Appl. No.: 928,126

[22] Filed: Sep. 12, 1997

[30] Foreign Application Priority Data

Mar. 24, 1995 [BE] Belgium .................................. 9500257
Mar. 19, 1996 [WO] WIPO ...................... PCT/NL96/00116

[51] Int. Cl.⁶ .................................................. C07D 209/48
[52] U.S. Cl. ............................................ 548/514; 564/301
[58] Field of Search ............................................... 548/514

[56] References Cited

FOREIGN PATENT DOCUMENTS

A-59-225147  12/1984  Japan .

OTHER PUBLICATIONS

Chemical Abstracts, vol. 103, No. 1, Abstract No. 6220p (1985).

*Primary Examiner*—Robert W. Ramsuer
*Attorney, Agent, or Firm*—Cushman Darby & Cushman IP Group of Pillsbury Madison & Sutro, LLP

[57] ABSTRACT

Method for the preparation of N-alkoxy-(tetra- or hexahydro)-phthalimide according to formula I

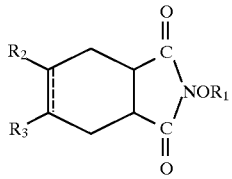

$R_1$ being methyl or ethyl and $R_2$ and $R_3$ being each independently of one another hydrogen or alkyl with 1–4 C atoms or $R_2$ and $R_3$ together with the carbon atom to which they are bonded forming a ring with 5 or 6 C atoms, wherein the salt of the corresponding N-hydroxy-(tetrahydro- or hexahydro)-phthalimide according to formula II:

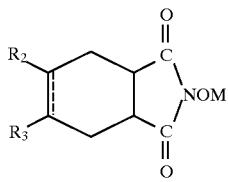

with $R_2$ and $R_3$ as defined above and M being an alkali metal, is brought into contact with $R_1Cl$ as alkylating agent, wherein $R_1$ has the aforementioned meaning.

The N-alkoxy-(tetra- or hexahydro)-phthalimide can afterwards be converted with the aid of hydroxylamine sulphate into the corresponding alkoxyamine after which the alkoxyamine obtained can be isolated. In this manner a simple and commercially attractive process for the preparation of O-(m)ethylhydroxylamine can be implemented.

6 Claims, No Drawings

METHOD FOR THE PREPARATION OF A N-ALKOXY-(TETRA-OR HEXAHYDRO)-PHTHALIMIDE AND METHOD FOR THE PREPARATION OF A N-ALKOXYAMINE

This is a Continuation of International Appln. No. PCT/NL96/00116 filed Mar. 19, 1996 which designated the U.S.

The invention relates to a method for the preparation of N-alkoxy-(tetra- or hexahydro)-phthalimide according to formula I

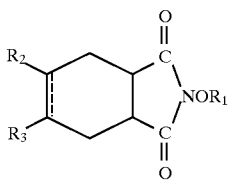

$R_1$ being methyl or ethyl and $R_2$ and $R_3$ being each independently of one another hydrogen or alkyl with 1–4 C atoms or $R_2$ and $R_3$ together with the carbon atom to which they are bonded forming a ring with 5 or 6 C atoms, wherein an alkali metal salt of the corresponding N-hydroxy-(tetrahydro- or hexahydro)-phthalimide according to formula II:

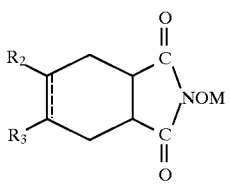

with $R_2$ and $R_3$ as defined above and M being an alkali metal, is brought into contact with a suitable alkylating agent. The dotted line represents the presence or absence of a double bond.

A method of this type is known from JP-A-84225147 in which N-methoxy-(tetra- and hexahydro)-phthalimide are prepared by alkylation with the aid of dimethyl sulphate.

A disadvantage of the known method is the use of dimethyl or diethyl sulphate since these sulphates are relatively costly. Furthermore, these sulphates are carcinogenic, which makes extra precautionary measures necessary. Besides, the use of these sulphates introduces a relatively high level of salt into the process.

The aim of the invention is to provide a method with which N-alkoxy-(tetra- or hexahydro)-phthalimide can be obtained in a simple, inexpensive and commercially attractive process that moreover entails low impact on the environment.

This is achieved according to the invention by using methyl chloride or ethyl chloride as alkylating agent.

The alkylated adducts, N-(m)ethoxy-(tetra- and hexahydro)-phthalimide are used especially in the preparation of alkoxyamines from hydroxylamine, the N atom being protected during the alkylation with the aid of a ring structure.

At the same time various processes are known in which other hydroxyimide ring structures are alkylated in an intermediate stage in the preparation of alkoxyamines. In general the most frequently mentioned alkylating agents are dialkyl sulphates and alkyl halides, the sulphates being more reactive than the much more expensive iodide, which in turn is much more reactive than the less expensive chloride. This proves to be especially important in alkylation with lower alkyl groups such as methyl and ethyl.

For practical applications, therefore, when a methyl or ethyl group has to be introduced via alkylation, the use of di(m)ethyl sulphate as alkylating agent is consistently described. Thus for example in JP-A-53144571 the alkylation of N-hydroxyphthalimide is described, and in the examples an ethyl group is introduced via alkylation with the aid of diethyl sulphate while all other, higher alkyl groups are introduced via alkylation with an alkyl halide—in particular an alkyl bromide if the alkyl halide is less reactive, for example if the alkyl is a higher saturated n-alkyl, and an alkyl chloride if the alkyl halide is more reactive, for example if alkyl stands for allyl or benzyl. The use of methyl chloride or methyl bromide as alkylating agent is even explicitly excluded here. Moreover, the applicant has found that the alkylation of N-hydroxyphthalimide with (m)ethyl chloride does not work.

In addition, from JP-A-59122465 the alkylation of N-hydroxy-5-norbornene-2,3-dicarboximide is known. Here too the alkylation by a methyl and ethyl group is performed with for example di(m)ethyl sulphate, while for the heavier alkyl groups the corresponding bromide (for example n-alkyl) or chloride (for example allyl or benzyl) is always used. Another disadvantage of the N-protecting group used in the method described here for the preparation of alkoxyamines is that this protecting group is expensive and moreover not biologically degradable, as a result of which this protecting group is very undesirable from the perspective of environmental protection.

The applicant has now found that in alkylation with the aid of (m)ethyl chloride good yields are nevertheless possible and that on this basis a commercially particularly attractive process for the preparation of (m)ethoxyamine is possible starting from a N-hydroxy-(hexahydro- or tetrahydro)-phthalimide. For cost reasons, preferably N-hydroxytetrahydrophthalimide is used.

Apart from the disadvantage of low reactivity, the use of methyl chloride and ethyl chloride has a number of practical advantages such as for example low toxicity, low cost, low molecular weight and lower production of salts.

The temperature at which the alkylation reaction is carried out is not critical and usually lies between 0° and 150° C.; preferably a temperature between 50° and 100° C. is maintained. In practice, alkylation with methyl chloride is on average conducted at a lower temperature than alkylation with ethyl chloride.

The pressure at which the alkylation reaction is carried out is not critical either. At atmospheric pressure the time needed for the alkylation reaction is relatively long. For this reason the alkylation reaction is preferably carried out at elevated pressure, for example at a pressure between 0.2 and 2 MPa. The upper limit is in fact determined by the excess (and hence losses) of methyl chloride which one is prepared to accept. In practice it is preferred to apply a pressure between 0.3 and 0.6 MPa, in which case alkylation with ethyl chloride will on average be carried out at a lower pressure than alkylation with methyl chloride. After the alkylation reaction the unreacted volatile methyl or ethyl chloride can for example be conveniently separated off by lowering the pressure to atmospheric pressure. Compared with alkylation with the aid of di(m)ethyl sulphate this consequently saves an additional processing operation. The (m)ethyl chloride liberated can be collected by dissolving it in a suitable solvent or by freezing it out at reduced temperature, after which it can be reused, which also reduces environmental impact.

The starting material, the alkali metal salt of N-hydroxy-(tetra- or hexahydro)-phthalimide, can for example be obtained by treating N-hydroxy-(tetra- or hexahydro)-phthalimide, if desired in situ at the time of the alkylation reaction, with an alkali metal hydroxide solution; or for example by bringing tetra- or hexahydrophthalic anhydride—which can for example be obtained by reaction of (substituted) butadiene and maleic anhydride—and hydroxylamine sulphate in water (eventually crude hydroxylamine sulphate in water in which also inorganic salts are present) into contact with alkali metal hydroxide solution. The reaction mixture obtained can be used as such in the alkylation reaction.

The alkylation reaction can be carried out in a homogeneous system, for example in an aqueous medium or in an organic solvent as described in JP-A-84225147 or in a two-phase system. Suitable organic solvents are solvents which are immiscible or only slightly miscible with water. Examples of such solvents are aromatic hydrocarbons such as for example toluene and benzene, esters such as for example ethyl acetate, ethers such as for example methyl tert-butyl ether, halogenated hydrocarbons such as for example chloroform and dichloromethane, and mixtures of such solvents.

When the alkylation reaction is carried out in two phases, a phase transfer catalyst (PTC) is usually used as described for example in Phase Transfer Catalysis, Third, Revised and Enlarged Edition, E. V. Dehmlow, S. S. Dehmlow, VCH Verlagsgesellschaft mbH Weinheim, NY Basle Cambridge Tokyo, in particular pp 65–79. Examples of suitable catalysts are quaternary ammonium salts, in particular tetraalkylammonium halides such as for example tetrabutylammonium chloride, benzyl-trimethylammonium chloride and cetyltrimethylammonium chloride. It has been found, however, that in a number of cases the alkylation yield did not fall when the PTC was omitted.

The reaction mixture obtained after the alkylation reaction can be worked up afterwards in known manner.

At the same time the invention relates to the preparation of O-(m)ethylhydroxylamine with use of the alkylation according to the invention. The reason for this is that it has been found that when an alkylation according to the invention is used, a particularly simple and commercially attractive process for the preparation of O-(m)ethylhydroxylamine is possible. This is particularly the case when the alkylation reaction is performed under elevated pressure. A particularly suitable embodiment of the method for the preparation of O-(m)ethylhydroxylamine proceeds, therefore, as described below.

As starting material an alkali metal salt, for example Na or K, of N-hydroxy-(tetra- or hexahydro)-phthalimide is used and is subjected to an alkylation reaction with the aid of (m)ethyl chloride. After the alkylation reaction the remaining (m)ethyl chloride is removed, for example by releasing the pressure. If the alkylation is performed in water, afterwards an organic solvent in which the alkylated adduct, obtained by alkylation of the phtalimide with (m)ethyl chloride, dissolves is added. The aqueous phase, which comprises a large part of the impurities, is separated off. Since the impurities present in the aqueous phase are biodegradable, this phase can simply be discharged. The organic phase, which comprises the alkylated adduct and the organic solvent, can be used as it is in the following step in which a two-phase system is obtained with the aid of a salt of hydroxylamine and a mineral acid, for example hydroxylamine sulphate (eventually crude hydroxylamine sulphate in water in which also inorganic salts are present) or hydroxylamine hydrochloride, and alkali metal hydroxide solution, for example KOH or NaOH. The organic phase consists in the main of the organic solvent and can be reused in the process as it is. From the aqueous phase, which comprises both O-(m)ethylhydroxylamine and the alkali metal salt of N-hydroxy-(tetra- or hexahydro)-phthalimide, O-(m)ethylhydroxylamine can be simply removed, for example by distillation. The O-(m)ethylhydroxylamine obtained can if desired be converted to a salt, for example with the aid of a mineral acid. The remaining aqueous phase can if desired be reused afterwards as a starting material in the alkylation.

The invention is explained further with reference to the following examples without, however, being limited to them.

EXAMPLE I

Preparation of N-hydroxytetrahydrophthalimide 25 g of hydroxylamine sulphate (0.152 mol, 99% pure) was dissolved in 100 g of water in a glass reactor. To this was added 47 g of tetrahydrophthalic anhydride (0.294 mol anhydride; 95% pure) after which 50 g of 25 wt % aqueous sodium hydroxide solution (0.313 mol) was added dropwise over a period of 15 minutes. Afterwards this reaction mixture was heated at 90° C. for two hours. After cooling to room temperature, the crystals formed were filtered off and dried under vacuum at 80° C. Yield: 44 g of N-hydroxytetrahydrophthalimide (0.264 mol); 89.6%.

EXAMPLE II

Preparation of the Sodium Salt of N-hydroxytetrahydrophthalimide 162 g of hydroxylamine sulphate (0.98 mol; 99% pure) was dissolved in 450 ml of water. To this was added 300 g of tetrahydrophthalic anhydride (1.89 mol, 96% pure). 160 g of 50 wt % aqueous sodium hydroxide solution was metered in over 15 minutes. After this the mixture was stirred for 1 hour at room temperature followed by stirring for 2 hours at 80° C. Afterwards the reaction mixture was cooled to 25° C. and 160 g of 50 wt % aqueous sodium hydroxide solution was again metered in. 1237 g of solution was obtained which contained 285 g of the sodium salt of N-hydroxytetrahydrophthalimide (1.51 mol). Yield: 80%.

EXAMPLE III

Synthesis of N-hydroxyhexahydrophthalimide 95 g of hexahydrophthalic anhydride (0.610 mol; 99% pure) was suspended in 130 ml of water in which 50 g (0.305 mol) of hydroxylamine sulphate was dissolved.

To this 100 g of 25 wt % aqueous sodium hydroxide solution was metered in over 10 minutes. Afterwards the reaction mixture was heated to 85° C. and kept at this temperature for 1 hour. After that the mixture was cooled to room temperature and the oil formed extracted with 2×100 ml of chloroform. The combined chloroform phases were dried over sodium sulphate and afterwards concentrated by evaporation. The oil obtained slowly solidified. Yield 99 g, 95% pure product (90% with respect to hexahydrophthalic anhydride).

EXAMPLE IV

Preparation of N-ethoxyhexahydrophthalimide

In an autoclave 60 g of a 20 wt % solution of the sodium salt of N-hydroxyhexahydrophthalimide (0.063 mol) and 5.0 g (0.078 mol) of ethyl chloride were mixed together. The mixture was heated to 100° C. After reaching this temperature the mixture was stirred for a further 5 hours while the temperature was maintained at 100° C. After 5 hours' reaction the excess ethyl chloride was blown out and the reaction mixture was discharged. The reaction product was extracted from the mixture with toluene. Gas chromatographic analysis of the toluene extract showed that the yield was 79% of N-ethoxyhexa-hydrophthalimide (0.050 mol).

EXAMPLE V

Preparation of N-ethoxytetrahydrophthalimide

In an autoclave a solution of 3.5 g of sodium methoxide (0.065 mol) in 40 ml of methanol, 11.0 g of N-hydroxytetrahydrophthalimide (0.066 mol) and 4.6 g (0.072 mol) of ethyl chloride were mixed together. The mixture was heated to 100° C. After reaching this temperature the mixture was stirred for a further 5 hours while the temperature was held at 100° C. After 5 hours' reaction the excess ethyl chloride was blown out and the reaction mixture was discharged. The reaction mixture comprised a large quantity of solid material. This was dissolved by the addition of water and the whole was afterwards extracted with toluene to obtain the product. Gas chromatographic analysis of the toluene extract showed that the yield was 74% of N-ethoxytetrahydrophthalimide (0.049 mol).

EXAMPLE VI

Preparation of N-ethoxytetrahydrophthalimide

In an autoclave 60 g of a 20 wt % solution of the sodium salt of N-hydroxytetrahydrophthalimide (0.063 mol) and 5.0 g (0.078 mol) of ethyl chloride were mixed together. The mixture was heated to 100° C. After reaching this temperature the mixture was stirred for a further 5 hours while the temperature was maintained at 100° C. After 5 hours' reaction the excess ethyl chloride was blown out and the reaction mixture was discharged. The reaction product was extracted from the mixture with toluene. Gas chromatographic analysis of the toluene extract showed that the yield was 84% of N-ethoxytetrahydrophthalimide (0.053 mol).

EXAMPLE VII

Preparation of N-ethoxytetrahydrophthalimide

In an autoclave 60 g of a 20 wt % solution of the sodium salt of N-hydroxytetrahydrophthalimide (0.063 mol), 20 ml of methyl tert-butyl ether and 5.0 g of ethyl chloride were mixed together. The mixture was heated to 100° C. After reaching this temperature the mixture was stirred for a further 5 hours while the temperature was maintained at 100° C. After 5 hours' reaction the excess ethyl chloride was blown out and the reaction mixture was discharged. The reaction mixture was composed of two liquid layers which were separated. The ether layer was analysed by gas chromatography. A yield of 81% of N-ethoxytetrahydrophthalimide (0.051 mol) was found.

EXAMPLE VIII

Preparation of N-methoxytetrahydrophthalimide 403 g of solution of the sodium salt of N-hydroxytetrahydrophthalimide (22.7 wt % solution in water), 100 ml of toluene and 2 ml of Arquat 16–50 (cetyltrimethylammonium chloride; 50 wt % solution in water) were combined in an autoclave. The mixture was heated to 80° C. and afterwards alkylated for 4 hours at this temperature under an atmosphere of 0.5 MPa of methyl chloride. On completion the excess methyl chloride was blown out and the reaction mixture was discharged. A two-phase system was produced. The lower aqueous layer contained mainly salts (inorganic drain). The toluene layer (169.7 g) comprised 42 wt % of alkylated adduct and 7.7 wt % of unreacted N-hydroxytetrahydrophthalimide. Yield of N-methoxytetrahydrophthalimide: 0.040 mol (82%).

EXAMPLE IX

Preparation of O-methylhydroxylamine I 15 g of N-methoxytetrahydrophthalimide (0.084 mol) was suspended in 50 ml of water. To this was added 6.9 g (0.042 mol) of hydroxylamine sulphate at 55° C. Over a period of 1 hour 26.9 g of 25 wt % aqueous sodium hydroxide solution (0.17 mol) was added. After stirring for 4 hours at 55° C. the temperature was increased and approximately 20 ml of the reaction mixture was distilled out.

The distillate was acidified with 37 wt % hydrochloric acid and concentrated by evaporation under reduced pressure in a rotary evaporator. On completion 5.8 g of O-methylhydroxylamine hydrochloride (0.070 mol) was obtained as a white precipitate (83%).

The residue after distillation was likewise acidified with concentrated hydrochloric acid and the precipitate formed was filtered off and dried in air. The recovered N-hydroxytetrahydrophthalimide amounted to 11 g (0.066 mol). Yield: 78%.

EXAMPLE X

Preparation of O-methylhydroxylamine II 179 g of the toluene layer derived from an alkylation performed analogously to the alkylation described in Example VIII was introduced into a 0.5 l reactor. The toluene layer comprised 78 g N-methoxytetrahydrophthalimide (0.43 mol) and 10.9 g N-hydroxytetrahydrophthalimide (0.065 mol). To this was added 37.2 g of hydroxylamine sulphate (0.227 mol) dissolved in 150 ml of water at 45° C. 37 g of 50 wt % sodium hydroxide solution was added over a period of 45 minutes. The reaction mixture was stirred for 2.5 hours (including the addition of the sodium hydroxide). After that 40.7 g of 50 wt.% sodium hydroxide (0.51 mol) was again metered in over 30 minutes. After 1 hour of further reaction the phases were separated. The toluene layer was washed with 40 g of water and the aqueous phases were combined with one another. The combined aqueous layers were distilled at atmospheric pressure. Approximately 100 g of distillate was collected, comprising 18.4 g of methoxyamine (0.39 mol). Yield: 91%.

The residue after distillation contained 78 g of the sodium salt of N-hydroxytetrahydrophthalimide (0.41 mol) which corresponds to 83% recovery.

We claim:

1. A method for the preparation of N-alkoxy-(tetra- or hexahydro)-phthalimide according to formula I

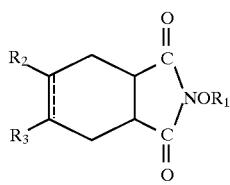

I $R_1$ being methyl or ethyl and $R_2$ and $R_3$ being each independently of one another hydrogen or alkyl with 1–4 C atoms or $R_2$ and $R_3$ together with the C atom to which they are bonded forming a ring with 5 or 6 C atoms, wherein the salt of the corresponding N-hydroxy-(tetrahydro- or hexahydro)-phthalimide according to formula II;

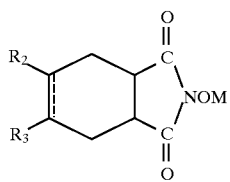

II with $R_2$ and $R_3$ as defined above and M being an alkali metal, is brought into contact with a suitable alkylating agent, characterized in that $R_1Cl$ is used as alkylating agent wherein $R_1$ has the aforementioned meaning.

2. The method of claim 1, characterized in that $R_2=R_3=H$.

3. The method of claim 1 or 2, characterized in that the alkylation reaction is carried out at a temperature between 50° and 100° C.

4. The method of claim 1, characterized in that the alkylation reaction is carried out under elevated pressure.

5. The method of claim 1, which further comprises converting the N-alkoxy-(tetra- or hexahydro)-phthalimide obtained into the corresponding alkoxyamine with the aid of a salt of hydroxylamine in the presence of alkali metal hydroxide solution; and isolating the alkoxyamine obtained.

6. The method of claim 5 which further comprises returning the alkali metal salt of N-hydroxy-(tetra- or hexahydro)-phthalimide obtained after the conversion with the aid of hydroxylamine to the alkylation reaction.

* * * * *